United States Patent
LoGuercio

(10) Patent No.: US 11,935,635 B2
(45) Date of Patent: Mar. 19, 2024

(54) MEDICAL INFORMATION LOOKUP PATCH AND METHOD THEREFOR

(71) Applicant: DJO, LLC, Carlsbad, CA (US)

(72) Inventor: Donald P. LoGuercio, Scottsdale, AZ (US)

(73) Assignee: DJO, LLC, Carlsbad, CA (US)

( * ) Notice: Subject to any disclaimer, the term of this patent is extended or adjusted under 35 U.S.C. 154(b) by 698 days.

(21) Appl. No.: 16/951,514

(22) Filed: Nov. 18, 2020

(65) Prior Publication Data

US 2021/0151152 A1 May 20, 2021

Related U.S. Application Data

(60) Provisional application No. 62/936,679, filed on Nov. 18, 2019.

(51) Int. Cl.
*G16H 10/65* (2018.01)
*A61B 5/00* (2006.01)
*G06K 7/14* (2006.01)

(52) U.S. Cl.
CPC .......... *G16H 10/65* (2018.01); *A61B 5/6833* (2013.01); *G06K 7/1417* (2013.01)

(58) Field of Classification Search
CPC .... G16H 10/65; A61B 5/6833; G06K 7/1417; G06K 19/00; G06K 19/04
USPC ........................................ 235/494, 487, 375
See application file for complete search history.

(56) References Cited

U.S. PATENT DOCUMENTS

| | | | |
|---|---|---|---|
| 2003/0212319 A1* | 11/2003 | Magill | A61B 5/6804 600/382 |
| 2009/0183299 A1* | 7/2009 | Conway | B65D 81/3897 283/56 |
| 2022/0125738 A1* | 4/2022 | Lafauci | G16H 20/10 |

FOREIGN PATENT DOCUMENTS

EP 2546784 A1 * 1/2013 ........... G06F 19/323

* cited by examiner

*Primary Examiner* — Edwyn Labaze
(74) *Attorney, Agent, or Firm* — Veros Legal Solutions, LLP

(57) ABSTRACT

A medical lookup patch, for application to a medical device, includes a substrate having a front, a back, and a perimeter edge defined therebetween. The patch includes an engagement element of a hook-and-loop engagement system on the back of the substrate, for engaging with a complemental engagement element on the medical device. The front of the substrate includes first, second, and third information areas. Brand information is displayed in the first information area, and instructive information is displayed in the second information area. Lookup information is displayed in the third information area and defines a machine-readable code which, when processed by a machine, directs the machine to display human-readable information different from the lookup information.

16 Claims, 6 Drawing Sheets

MEDICAL INFORMATION LOOKUP PATCH AND METHOD THEREFOR

CROSS-REFERENCE TO RELATED APPLICATIONS

This application claims the benefit of U.S. Provisional Application No. 62/936,679, filed Nov. 18, 2019, which is hereby incorporated by reference.

FIELD

The present specification relates generally to medical devices, and more particularly to medical devices for communicating and looking up information.

BACKGROUND

Patients who undergo surgery have a lot of information to remember. They are often discharged with piles of paper through which to sort. They may be given special post-operative instructions which add to, expand on, or deviate from those provided in person. Remembering proper care and recovery routines is an additional burden on a patient recovering from surgery. An improved way to provide patients with easily-accessible, personalized recovery information is needed.

SUMMARY

A medical lookup patch, for application to a medical device, includes a substrate having a front, a back, and a perimeter edge defined therebetween. The patch includes an engagement element of a hook-and-loop engagement system on the back of the substrate, for engaging with a complemental engagement element on the medical device. The front of the substrate includes first, second, and third information areas. Brand information is displayed in the first information area, and instructive information is displayed in the second information area. Lookup information is displayed in the third information area and defines a machine-readable code which, when processed by a machine, directs the machine to display human-readable information different from the lookup information.

In another embodiment, a method for creating and using a medical lookup patch with a medical device includes an owner providing a web server, contracting with a health worker to provide a medical lookup patch to the health worker, and collecting from the health worker contact information and medical care information. The method further includes building and hosting a microsite for the health worker which features the contact information and medical care information. The method still further includes encoding lookup instructions for the microsite in the machine-readable code and providing a medical lookup patch displaying the machine-readable code to the health worker for distribution to patients thereof. The method yet further includes the health worker applying the medical lookup patch to a medical device provided to one of the patients, the one of the patients reading the machine-readable code on the medical lookup patch with a machine, and the machine processing the machine-readable code and thereby being directed to display human-readable information including the contact and medical care information.

The above provides the reader with a very brief summary of some embodiments described below. Simplifications and omissions are made, and the summary is not intended to limit or define in any way the disclosure. Rather, this brief summary merely introduces the reader to some aspects of some embodiments in preparation for the detailed description that follows.

BRIEF DESCRIPTION OF THE DRAWINGS

Referring to the drawings.

DETAILED DESCRIPTION

Figure 2:
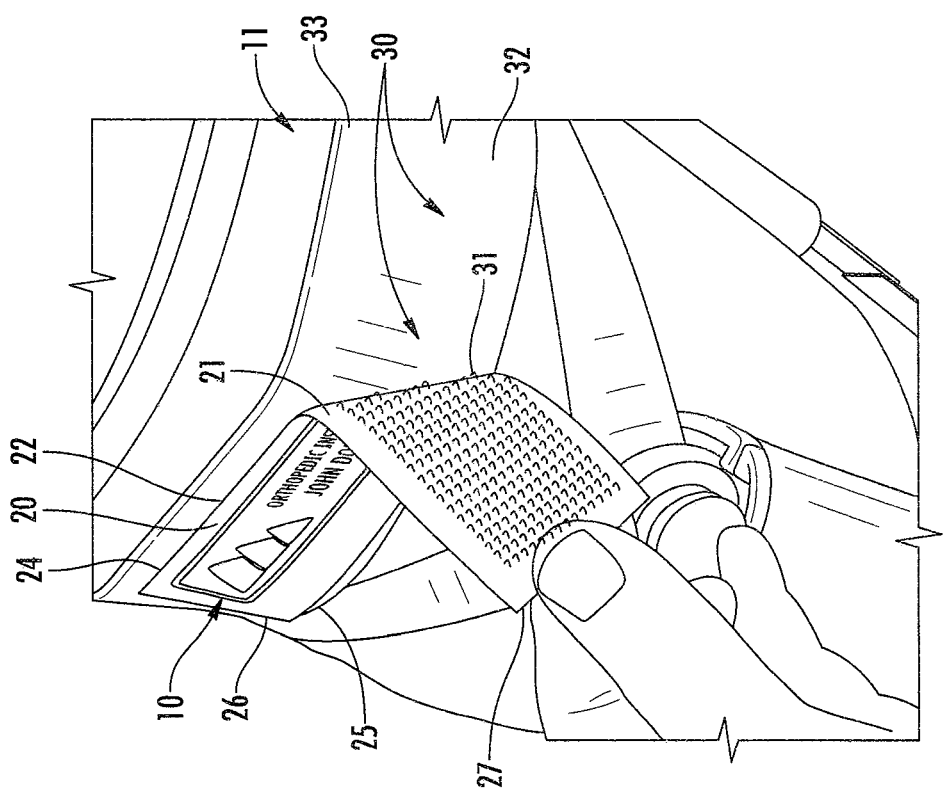
FIGS. 1 and 2 are top perspective views of a medical information lookup patch applied to a medical device.

Reference now is made to the drawings, in which the same reference characters are used throughout the different figures to designate the same elements. Briefly, the embodiments presented herein are preferred exemplary embodiments and are not intended to limit the scope, applicability, or configuration of all possible embodiments, but rather to provide an enabling description for all possible embodiments within the scope and spirit of the specification. Description of these preferred embodiments is generally made with the use of verbs such as "is" and "are" rather than "may," "could," "includes," "comprises," and the like, because the description is made with reference to the drawings presented. One having ordinary skill in the art will understand that changes may be made in the structure, arrangement, number, and function of elements and features without departing from the scope and spirit of the specification. Further, the description may omit certain information which is readily known to one having ordinary skill in the art to prevent crowding the description with detail which is not necessary for enablement. Indeed, the diction used herein is meant to be readable and informational rather than to delineate and limit the specification; therefore, the scope and spirit of the specification should not be limited by the following description and its language choices.

Figure 1:
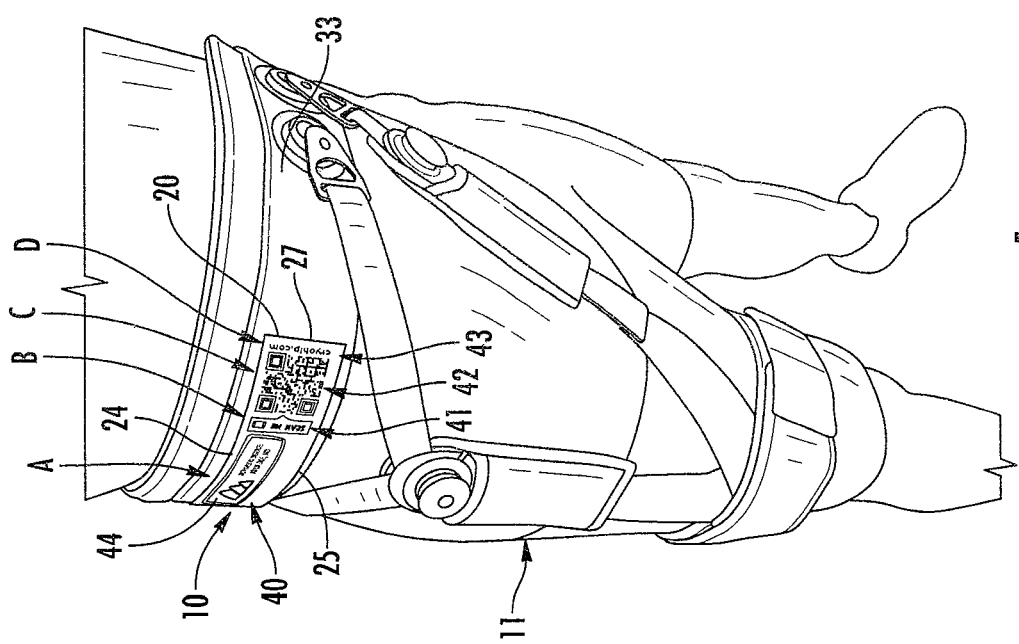

FIG. 1 is a perspective view illustrating a medical information lookup patch 10 (hereinafter, the "patch 10") applied to a medical device 11, namely, a hip orthosis. The patch 10 displays information, some of which is readable by human eye and some of which is readable by a computer. When a patient wearing the device desires to remember routines for his post-operative care, recovery, or medical device 11, he can read the patch 10, scan it with a phone, and be provided with specific information.

Three embodiments of the patch 10 are shown in the drawings. The embodiments are similar but not identical. FIGS. 1 and 2 show a first embodiment of the patch 10, identified here with the reference character 10. The patch 10 includes a substrate 20 having a front 21 and an opposed back 22, both of which are flat. The front 21 and back 22 meet at and define a perimeter edge 23 therebetween. The substrate 20 is constructed preferably from a strong, durable, flexible material, such as nylon, thick cotton, webbing, or the like. The patch 10 can be used with different medical devices 11 and applied in different locations, overlying different structures, shapes, and contours, and so the characteristics of flexibility and durability allow it to be so placed without inadvertently coming loose from the medical devices 11. Further, the patch 10 can be repeatedly removed and re-applied without destroying the information displayed on the patch 10.

The substrate 20 is preferably, though not necessarily, rectangular, such that it has a long upper edge 24, a long parallel lower edge 25, and two side edges 26 and 27 parallel to each other and perpendicular to the upper and lower edges 24 and 25 each. The length and arrangement of these edges 24-27 with respect to each other defines the perimeter edge 23 as a rectangle.

The back 22 of the substrate 20 carries one engagement element of an engagement system 30. Preferably, and as shown in the embodiment in FIG. 2, the back 22 carries a hook element 31 of a hook-and-loop engagement system 30. The hook elements 31 cover the entire back 22 and are directed outward, ready to be applied to and engage with complemental loop elements 32.

Typically, medical devices 11 have soft, pliant fabric materials on the outside, which are more comfortable for the patient to wear during a recovery period. Such soft and pliant fabrics generally have loop elements 32 complemental to the hook elements 31. The outer surface of the medical device 11 preferably carries or is formed with the complemental loop element 32 of the hook-and-loop engagement system 30. In cases in which the medical device 11 does not carry a complemental loop element 32, the medical device 11 may be fitted with a strip of material having loops 32 directed outwardly. The back 22 of the substrate 20 may be engaged across the outer surface of the medical device 11 generally anywhere that is covered by the loop element 32. Here, a strap 33 near the top of the medical device 11 is a soft and pliant fabric finished with loops 32 which are sufficient for the hooks 31 to engage.

The front 21 of the substrate 20 is smooth and flat, without significant features rising or receding from the front 21. Information is printed on the front 21 in separate zones or areas. Referring to FIG. 1 and to FIG. 3 (which shows identical readable information), there are four distinct information areas A, B, C, and D. Each is a different size and contains different information for different purposes.

The first information area A contains brand information 40. The brand information 40 displays branding and identification information about the manufacturer or source of the patch 10. This information 40 is presented in the human-readable form of Latin letters spelling English-language words. These words are arranged in a horizontal orientation, aligned between the side edges 26 and 27. As shown in the drawings, the first information area A identifies ORTHOPEDIC INSTITUTE as the manufacturer or source of the patch 10. Further, area A contains the words JOHN DOE, MD, indicating that the patch 10 is for use with a medical device 10 provided by John Doe, MD. In other embodiments, the information in this first area A may also display information for the medical device 11 to which the patch 10 is attached. The information area A is centered between the upper and lower edges 24 and 25 and is proximate the side edge 26. It is a large rectangular area, extending from the side edge 26 to beyond the middle of the front 21 between the side edges 26 and 27.

The second information area B contains instructive information 41 in an area much smaller than that of area A. The information area B is slender, extending vertically entirely between the upper and lower edges 24 and 25 but having a width between the edges 26 and 27 which is approximately one-fifth its height. The second information area B is adjacent the first information area A. The instructive information 41 in the second information area B is presented in the human-readable form of Latin letters spelling English-language words, along with icons. These words and icons are arranged in a vertical direction, aligned between the upper and lower edges 24 and 25. As shown in the drawings, the second information area B instructs the patient to SCAN ME, or to scan the patch 10. Further, the information area B includes an icon of a mobile phone to instruct the patient to use his mobile phone to scan the patch 10. A graphical box surrounding the human-readable information includes a small arrow or triangle pointing to the third information area C.

Adjacent the second information area B is the third information area C containing lookup information 42. The second information area B is rectangular and roughly square, extending between the upper and lower edges 24 and 25 of the patch 10 and similarly far in width between the third information area C and the fourth information area D proximate the side 27. The third information area C contains machine-readable code or information. In other words, the lookup information 42 in the second information area B is preferably encoded and thus not readable by a human.

As shown in the embodiments of these drawings, the lookup information 42 in the third information area C is in the machine-readable form of a two-dimensional matrix or barcode. Here, the drawings show a QR code as one non-limiting example of the lookup information 42. When scanned by an electronic device such as an Internet-connected phone, computer, or tablet with appropriate software, the electronic device decodes the QR code and opens a browser to provide the patient with medical information, as will be explained. In other embodiments, the machine-readable information 42 may be a two-dimensional code such as a barcode for displaying encoded information in a way that only a machine can read it. A QR code is preferred because the QR code is a dynamic link to content which can be edited later in time.

Proximate the side edge 27, and between the side edge 27 and the third information area C, is the fourth information area D containing additional information 43. Like the second, the fourth information area D is slender, extending vertically entirely between the upper and lower edges 24 and 25 but having a width between the edges 26 and 27 which is approximately one-fifth its height. The additional information 43 in the fourth information area D is presented in the human-readable form of Latin letters. Here, the fourth information area D displays a domain name or URL, arranged in a vertical direction and aligned between the upper and lower edges 24 and 25. This fourth information area D presents help information for the patient should he have difficulty scanning the patch 10 to look up information. The patient can type the URL into a browser and access additional information about how to use the patch 10, including contact information for the manufacturer. In some embodiments, this fourth information area D may not be included, may be left blank, or may be filled with information which is custom to the doctor, clinic, or health worker providing the patch 10.

The brand, instructive, lookup, and additional information 40-43 is easily readable on the front 21 of the patch 10. In the embodiment of FIGS. 1 and 2, the substrate 20 itself is preferably black or another very dark color. Ink 44 is then applied directly to the front 21 in each of the information areas A-D. The ink 44 is applied separately in each information area A-D, such that it does not overlap from one area into another, and such that a different color of ink 44 may be used in each area to further distinguish the information areas A-D from each other. Preferably, the ink 44 is a white ink, thereby providing a high contrast on the black front 21 of the substrate 20, but the ink 44 may also be another high-contrast color such as bright yellow, neon green, or the like. The stark, high contrast color of the ink 44 allows a patient to read and scan the information areas A-D even in low light conditions, or even if the patient has poor eyesight. In some embodiments, if the substrate 20 is a color other than black or a very dark color, the ink 44 chosen may be a dark color. For example, if the substrate 20 is white, the ink 44 may preferably be black. Of course, other colors of ink 44 may be used, but ones which provide a high contrast against the color of the front 21 of the substrate 20 are preferred.

Figure 3:
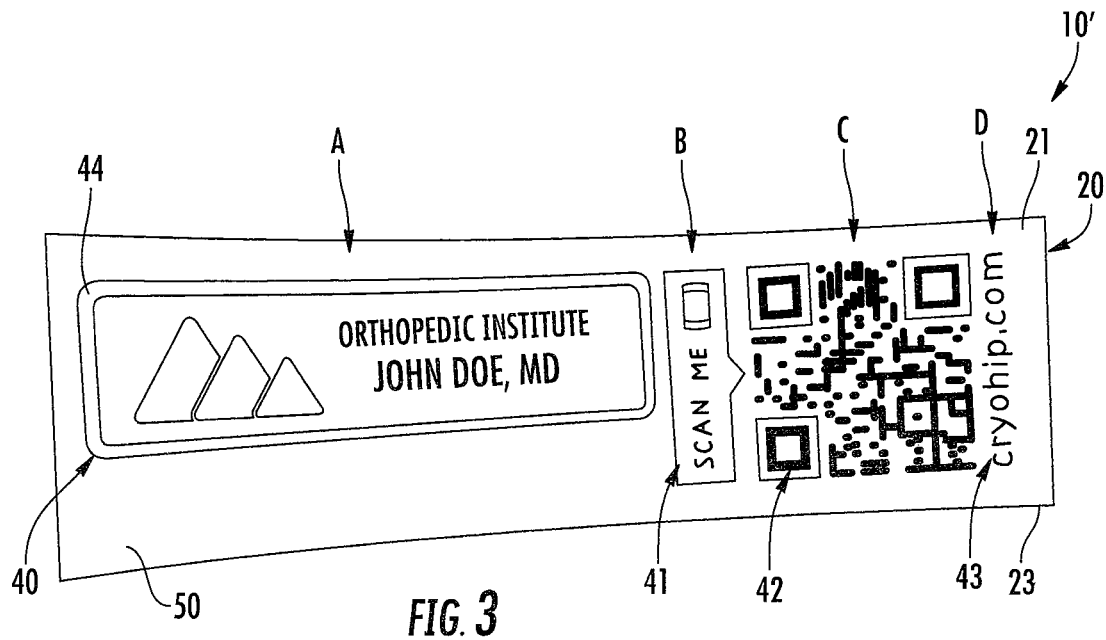
FIG. 3 is a perspective view of another embodiment of a medical information lookup patch.

FIG. 3 illustrates an alternate embodiment of the patch identified with the reference character 10'. The patch 10' is nearly identical to the patch 10 of FIGS. 1 and 2, and for that reason the same names and reference characters are used to identify the same structural elements and features. As such, it has a substrate 20, front 21, back 22, perimeter edge 23, upper edge 24, lower edge 25, side edge 26, side edge 27, hook element 31 of the engagement system 39, information areas A-D, brand information 40, instructive information 41, lookup information 42, and additional information 43, and the ink 44. Not all of these reference characters are shown in FIG. 3, as the reader should readily understand their location and arrangement from the earlier description relating to FIGS. 1 and 2.

Unlike the patch 10, however, the patch 10' has a flood or first layer of ink 50 which is applied directly to the front 21 of the substrate and across the front 21 entirely within the perimeter edge 23. This first layer of ink 50 is preferably black or a very dark color. The ink 44 is then applied as a second layer over the first layer of ink 50, and is applied separately in each of the information areas A-D. When the second layer of ink 44 is white, it presents with a very high contrast against the first layer of ink 50. This is generally a higher-contrast presentation of the ink 44 than occurs in the patch 10 where the ink 44 is printed directly onto the front 21 of the substrate 20. Further, the first layer of ink 50 establishes an impermeable barrier, thereby preventing the ink 44 from bleeding into the front 21 of the substrate 20.

Figure 4:
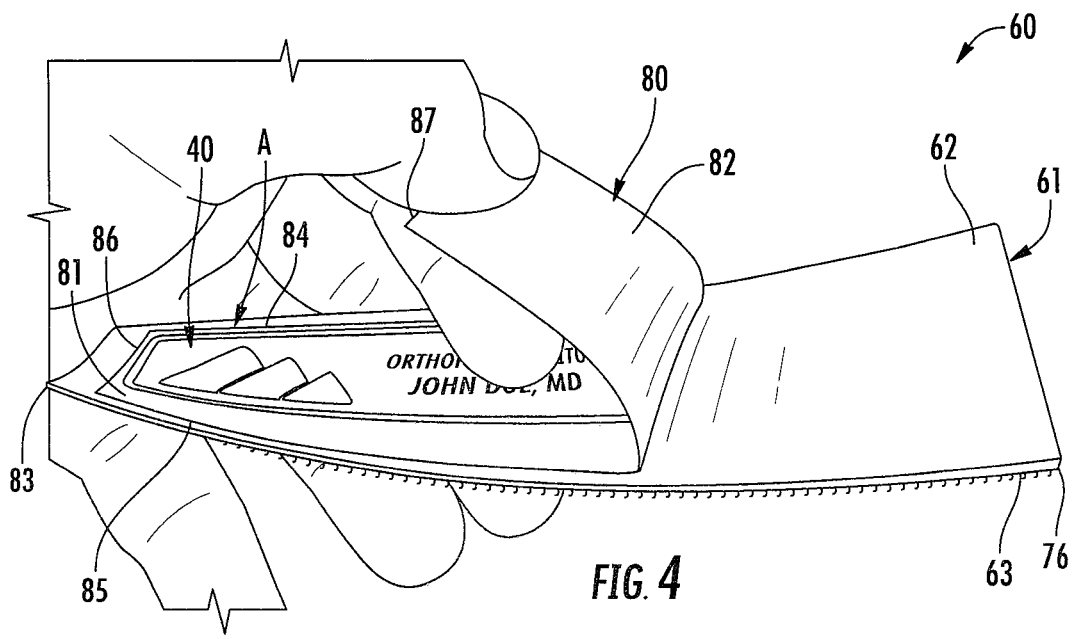
FIG. 4 is a perspective view of yet another embodiment of a medical information lookup patch.

FIG. 4 illustrates another embodiment of the patch, identified with the reference character 60. This patch 60 is similar but not identical to the patches 10 and 10'. The patch 60 is also useful for application to a medical device 11, and also displays different information, readable by human eye and readable by machine. The patch 60 includes a substrate 61 having a front 62 and an opposed back 63, both of which are flat. The front 62 and back 63 meet at and define a perimeter edge 64 therebetween. The substrate 61 is constructed preferably from a strong, durable, flexible material, such as nylon, thick cotton, webbing, or the like. Like the patch 10, the patch 60 can be repeatedly removed from and re-applied to the medical device 10 without destroying the information displayed on the patch 60.

The substrate 61 is preferably, though not necessarily, rectangular, such that it has a long upper edge 70, a long parallel lower edge 71, and two side edges 72 and 73 parallel to each other and perpendicular to the upper and lower edges 70 and 71 each. The length and arrangement of these edges 70-73 with respect to each other defines the perimeter edge 64 as a rectangle.

The back 63 of the substrate 61 carries one engagement element of an engagement system. Preferably, and similarly to the embodiment in FIG. 2, the back 63 carries a hook element 76 of a hook-and-loop engagement system. The hook elements 76 cover the entire back 63 and are directed outward, ready to be applied to and engage with complemental loop elements on the medical device 11.

The front 62 of the substrate 61 is flat, without significant features rising or receding from the front 62. The front 62 is also preferably smooth, but in some embodiments may have a texted or roughened surface. An applique 80 is applied to the front 62. The applique 80 displays the human-readable and machine-readable information.

The applique 80 has a front 81 and an opposed back 82, both of which are flat and smooth. The front 81 and back 82 meet at and define a perimeter edge 83 therebetween. The applique 80 is constructed from a strong, durable, flexible, and thin material, such as nylon, vinyl, plastic, or the like. The applique 80 is preferably permanently applied to the front 62 of the substrate 61.

The applique 80 is preferably, though not necessarily, rectangular, such that it has a long upper edge 84, a long parallel lower edge 85, and two side edges 86 and 87 parallel to each other and perpendicular to the upper and lower edges 84 and 85. The length and arrangement of these edges 84-87 with respect to each other defines the perimeter edge 83 as a rectangle. The back 82 of the applique 80 carries an adhesive for permanent application to the front 62 of the substrate 61. FIG. 4 shows the applique 80 being applied to the substrate 61. The applique 80 corresponds in shape and is just smaller in size with respect to the substrate 61, and so the applique 80 is centered and thus registered within the perimeter edge 64 of the substrate 61.

The front 81 of the applique 80 is smooth and flat, without significant features rising or receding from the front 81. Information is printed on the front 81 in separate zones or areas, the same information areas A-D as the ones shown in FIG. 3 for the patch 10', and so explanation of their location, size, shape, and function is unnecessary here. The information area A can be seen in FIG. 4 displaying the brand information 40.

The applique 80 itself is preferably black or another very dark color. Ink 90 is then applied directly to the front 81 in each of the information areas A-D on the applique 80. The ink 90 is applied separately in each information area A-D, such that it does not overlap from one area into another, and such that a different color of ink 90 may be used in each area to further distinguish the information areas A-D from each other. Preferably, the ink 90 is a white ink, thereby providing a high contrast on the black front 81 of the applique 80, but the ink 90 may also be another high-contrast color such as bright yellow, green, or the like. The stark, high-contrast color of the ink 90 allows a patient to read and scan the information areas A-D even in low light conditions, or even if the patient has poor eyesight. In some embodiments, if the applique 80 is a color other than black or a very dark color, the ink 90 chosen may be a dark color. For example, if the applique 80 is white, the ink 90 may preferably be black. Of course, other colors of ink 90 may be used, but ones which provide a high contrast against the color of the front 81 of the applique 80 are preferred.

In other embodiments of the applique 80, the applique 80 includes a floor or first layer of ink 91 which is applied directly to the front 81 of the applique 80 across the front 81 entirely within the perimeter edge 83. This first layer of ink 91 is preferably black or a very dark color. The ink 90 is then applied as a second layer over the first layer of ink 91, and is applied separately in each of the information areas A-D covering the entire front 81. When the second layer of ink 90 is white, it presents with a very high contrast against the first layer of ink 91. The first layer of ink 91 establishes an impermeable barrier, thereby preventing the ink 90 from bleeding into the front 81 of the applique 80.

Figure 5:
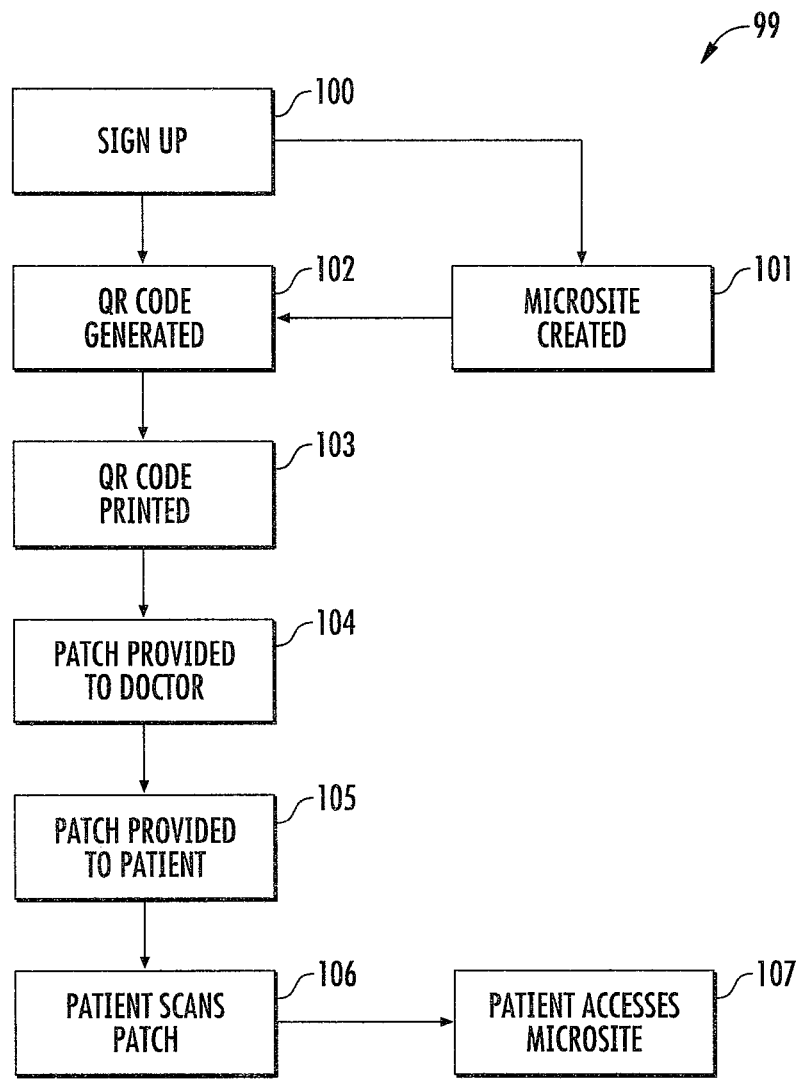
FIG. 5 is a flowchart illustrating steps of creating and using a medical information lookup patch.

Turning now to FIG. 5, a generalized flow chart of the operation of a system 99 operated by an owner for doctors and patients using one of the patches 10, 10', or 60 with a medical device 11 is shown. Any of the patches 10, 10', and 60 are suitable for use in the system 99; the description below describes use of the system 99 with the patch 10, but the operation of the system 99 is no different for patches 10' or 60.

The system 99 operates on an Internet-connected web server. Initially, an owner of the system 99 purchases, prepares, and runs the web server. The web server may be a single desktop computer, a server computer, a series of networked computers, or remotely-hosted or virtually-hosted server space. The owner of the system 99 makes the web server available for the use of its customers, typically doctors, medical clinics, physical therapists, and other health workers and providers. These are generally identified below with the term "health worker."

The owner of the system 99—or sales representatives for the owner—establishes contact with and tries to sign the health worker to a contract. If the health worker agrees, the owner contracts with the health worker to provide the patch 10 to the health worker. The health worker provides the patch 10 to its patients.

Figure 6A:
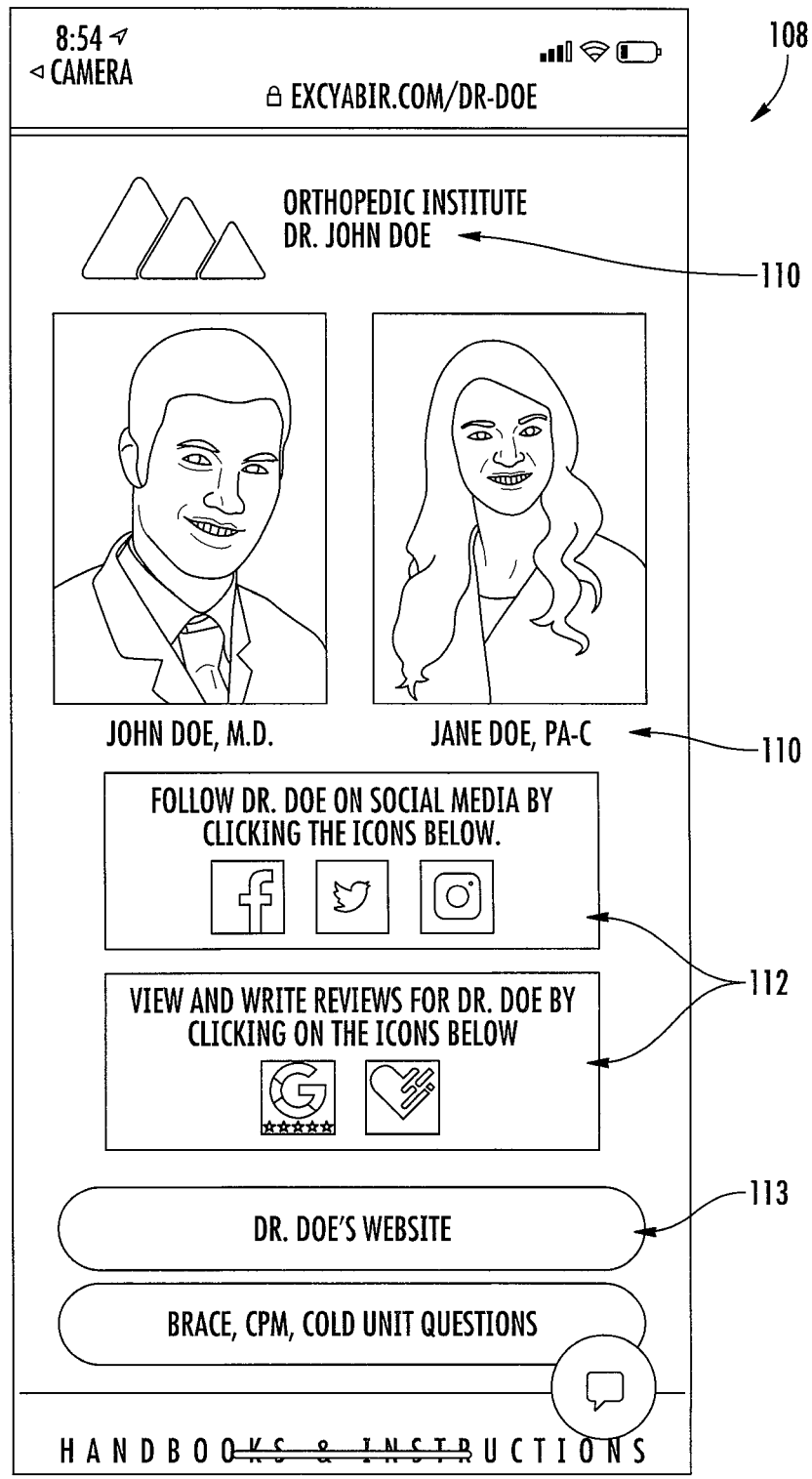
FIGS. 6A-6C are illustrations of a microsite for use within the system of FIG. 5.
Figure 6B:
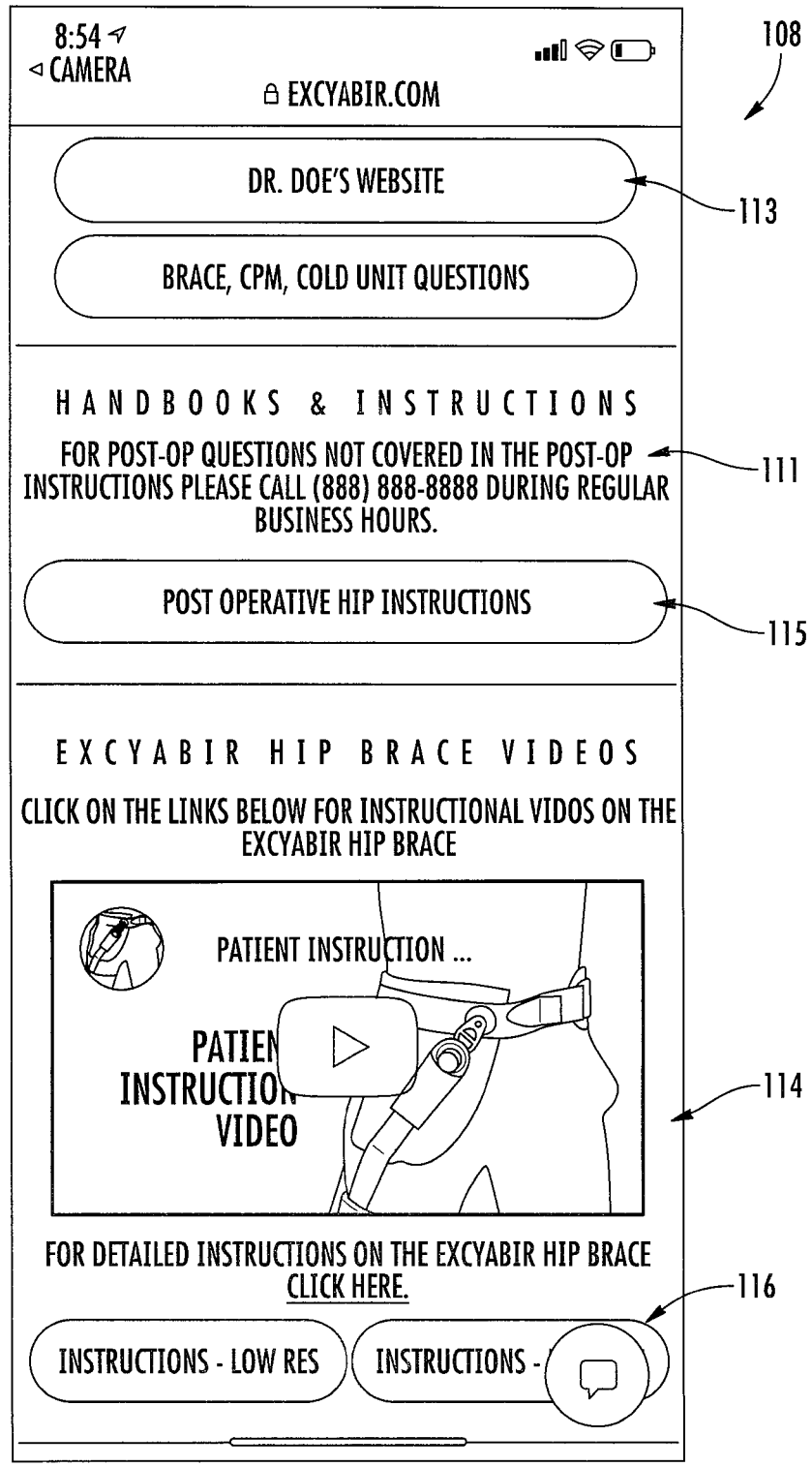
Figure 6C:
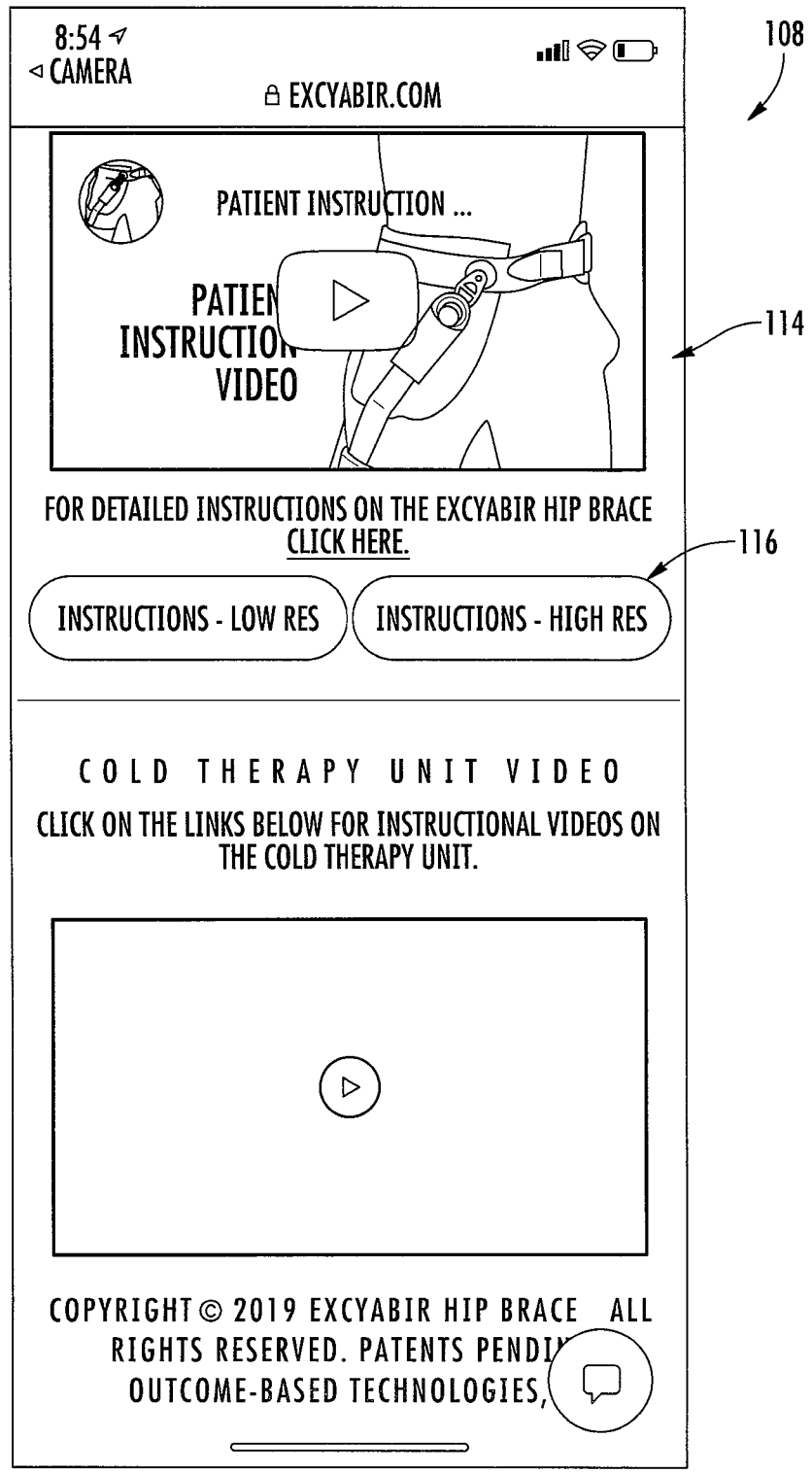

Initially, at step 100, a health worker is signed up to participate in the system 99. Typically, the owner or its sales representative contacts the health worker and provides information about the system 99, the medical device 11, and the patch 10. In other cases, the health worker may on its own request to join the system 99. When a health worker signs up with the system 99 (step 100), the owner of the system 99 creates a microsite 108 for the health worker (step 101). A microsite 108 is a website providing personalized information about the health worker, about the medical device 10, and about the recovery routines. An example of a microsite 108 is seen in FIGS. 6A-6C. The microsite 108 is hosted by the owner but has an outwardly-facing appearance of being provided by the health worker.

To build the microsite 108 in step 101, the system 99 needs contact information for the health worker and medical care information. As such, when the health worker contracts with the owner, or just thereafter, the owner collects contact and medical care information from the health worker. The collected contact information includes biographical information 110 about the health worker such as the names of doctors, nurses, therapists, and other health workers. The contact information further includes both general and specific phone and address information 111 for each health worker, as well as any social media information 112 that may be available for the health worker. The contact information typically also includes website information 113 for the health worker, such as domain names, URLs, hyperlinks, or dynamic buttons for accessing the health worker's main websites.

The collected medical care information includes answers to frequent questions concerning the medical procedures provided by the health worker, answers to frequent questions 114 concerning the medical devices provided by the health worker, medical care instructions 115 for each procedure and recovery therefrom, and instructions 116 for use of the medical devices provided by the health worker.

Each procedure and medical device is then categorized separately such that specific information for each procedure, medical device, and recovery is not associated or commingled with information for others. A unique sub-account is created with the health worker's account on the web server for each procedure provided by the health worker. Preferably, a unique micro-site is created for each medical procedure, corresponding to that unique sub-account.

Each microsite 108 has a domain name or URL associated with it. Once the microsite 108 is created at step 101, lookup instructions for the microsite 108 are encoded into a machine-readable code. Generally, this is a QR code, and so the description hereinafter will refer to a QR code for the machine-readable code. Thus, at step 102, the QR code is generated. The QR code contains an encoded instruction to a machine or mobile device to open a browser to the unique URL for the microsite 108.

The patch 10 is then created, preferably by the owner. The QR code is printed onto the patch 10 in information area C as the lookup information 42 (step 103). The human-readable information is also printed on the patch 10 in areas A, B, and D. The patch 10 is then provided to the health worker (step 104). Typically, the health worker receives many patches 10 at once, generally along with the medical devices 11 ordered.

When a patient undergoes a procedure and needs a medical device 11, the health worker provides the medical device 11 to him (step 105). The health worker additionally provides the patch 10 with the medical device 11, preferably applying the patch directly to the medical 11 before distributing it to the patient. The health worker explains that the patch 10 can be scanned if the patient has questions about recovery or other medical issues related to the device 11.

If the patient does have questions after leaving the care of the health worker, he reads the patch (step 106) with his Internet-connected phone, computer, tablet, or like machine or device. When the device scans the machine-readable lookup information 42, the device processes the machine-readable lookup information 42 into instructions which direct the machine to load and display the microsite 108 on a browser. The patient can then browse the contact and medical care information as desired (step 107). The health worker may have one only microsite 108 if he provides just one type of medical device 11 and procedure. However, if the health worker provides different medical devices 11 and procedures, the health worker may have several microsites 108, each corresponding to the respective device 11 and procedure. In such a case, the health worker also provides the patient with the patch 10 carrying machine-readable information 42 corresponding to the medical device 11 and procedure.

A preferred embodiment is fully and clearly described above so as to enable one having skill in the art to understand, make, and use the same. Those skilled in the art will recognize that modifications may be made to the description above without departing from the spirit of the specification, and that some embodiments include only those elements and features described, or a subset thereof. To the extent that modifications do not depart from the spirit of the specification, they are intended to be included within the scope thereof.

What is claimed is:

1. A medical lookup patch, for application to a medical device, comprising:
  a substrate having a front, a back, and a perimeter edge defined therebetween;
  an engagement element of a hook-and-loop engagement system on the back of the substrate, for engaging with a complemental engagement element on the medical device;

the front of the substrate includes first, second, and third information areas;

brand information is displayed in the first information area;

instructive information is displayed in the second information area;

lookup information is displayed in the third information area, the lookup information defining a machine-readable code which, when processed by a machine, directs the machine to display human-readable information different from the lookup information; and a first layer of ink applied directly to the front of the substrate, across the front entirely within the perimeter edge; and a second layer of ink applied over the first layer of ink.

2. The medical lookup patch of claim 1, wherein the brand, instructive, and lookup information are each formed from a layer of ink applied directly to the front of the substrate.

3. The medical lookup patch of claim 1, wherein the second layer of ink is separated in each of the first, second, and third information areas.

4. The medical lookup patch of claim 1, wherein the first, second, and third information areas are each of different sizes.

5. The medical lookup patch of claim 1, wherein the substrate comprises a flexible sheet of fabric.

6. A medical lookup patch, for application to a medical device, comprising:

a substrate having a front and a back;

an engagement element of a hook-and-loop engagement system on the back of the substrate, for engaging with a complemental engagement element on the medical device;

an applique having a front, a back, and a perimeter edge defined therebetween, wherein the back of the applique is applied to the front of the substrate;

the front of the applique includes first, second, and third information areas;

brand information is displayed in the first information area;

instructive information is displayed in the second information area;

lookup information is displayed in the third information area, the lookup information defining a machine-readable code which, when processed by a machine, directs the machine to display human-readable information different from the lookup information; and a first layer of ink applied directly to the front of the applique, across the front entirely within the perimeter edge; and a second layer of ink applied over the first layer of ink.

7. The medical lookup patch of claim 6, wherein the brand, instructive, and lookup information are each formed from a layer of ink applied directly to the front of the applique.

8. The medical lookup patch of claim 6, wherein the second layer of ink is separated in each of the first, second, and third information areas.

9. The medical lookup patch of claim 6, wherein the first, second, and third information areas are each of different sizes.

10. The medical lookup patch of claim 6, wherein the substrate comprises a flexible sheet of fabric.

11. A method for creating and using a medical lookup path with a medical device, the method comprising: an owner providing a web server; the owner contracting with a health worker to provide a medical lookup patch to the health worker; wherein the medical lookup patch comprises: a substrate having a front, a back, and a perimeter edge defined therebetween; an engagement element of a hook-and-loop engagement system on the back of the substrate, for engaging with a complemental engagement element on the medical device; the front of the substrate includes first, second, and third information areas; brand information is displayed in the first information area; and instructive information is displayed in the second information area; lookup information is displayed in the third information area, which, when processed by the machine, directs the machine to display the human-readable information; an applique having a front, a back, and a perimeter edge defined therebetween, wherein the back of the applique is applied to the front of the substrate; the front of the applique is smooth and includes first, second, and third information areas; brand information is displayed in the first information area; instructive information is displayed in the second information area; and lookup information is displayed in the third information area, which, when processed by the machine, directs the machine to display the human-readable information (41 collecting from the health worker contact information and medical care information; building and hosting a microsite for the health worker featuring the contact information and medical care information; encoding lookup instructions for the microsite in the machine-readable code; providing a medical lookup patch displaying the machine-readable code to the health worker for distribution to patients thereof; the health worker applying the medical lookup patch to a medical device provided to one of the patients; and the one of the patients reading the machine-readable code on the medical lookup patch with a machine, and the machine processing the machine-readable code and thereby being directed to display human-readable information including the contact and medical care information.

12. The method of claim 11, wherein the contact information includes at least one of:

biographical information about the health worker;

phone and address information for the health worker;

social media information for the health worker; and website information for the health worker.

13. The method of claim 11, wherein the medical care information includes at least one of:

answers to frequent questions concerning a medical procedure;

answers to frequent questions concerning the medical device;

medical care instructions for the procedure and recovery therefrom; and instructions for use of the medical device.

14. The medical lookup patch of claim 11, wherein the brand, instructive, and lookup information are each formed from a layer of ink applied directly to the front of the substrate.

15. The medical lookup patch of claim 11, further comprising:

a first layer of ink applied directly to the front of the applique, across the front entirely within the perimeter edge; and a second layer of ink applied over the first layer of ink.

16. The medical lookup patch of claim 11, further comprising:
   a first layer of ink applied directly to the front of the applique, across the front entirely within the perimeter edge; and
   a second layer of ink applied over the first layer of ink.

\* \* \* \* \*